United States Patent [19]
Kratzer et al.

[11] Patent Number: 6,159,741
[45] Date of Patent: Dec. 12, 2000

[54] PROCESS FOR MEASURING BLOOD PLATELET AGGREGATION OR BLOOD COAGULATION

[75] Inventors: Michael Kratzer, München; Volker Freiherr Von Der Goltz, Seeon, both of Germany

[73] Assignees: Dr. Michael Kratzer GmbH, München; VDG-Von Der Goltz GmbH, Seeon, both of Germany

[21] Appl. No.: 09/180,070

[22] PCT Filed: Apr. 30, 1997

[86] PCT No.: PCT/EP97/02230

§ 371 Date: Dec. 11, 1998

§ 102(e) Date: Dec. 11, 1998

[87] PCT Pub. No.: WO97/41431

PCT Pub. Date: Nov. 6, 1997

[30] Foreign Application Priority Data

Apr. 30, 1996 [DE] Germany .......................... 196 17 407

[51] Int. Cl.[7] .................................................. G01N 33/86
[52] U.S. Cl. ............................... 436/69; 422/73; 73/64.41
[58] Field of Search ................................. 436/69; 422/73; 73/64.41

[56] References Cited

U.S. PATENT DOCUMENTS

| | | | |
|---|---|---|---|
| 3,911,728 | 10/1975 | Fixot | 73/55 |
| 4,604,894 | 8/1986 | Kratzer et al. | 73/64.1 |
| 4,780,418 | 10/1988 | Kratzer | 436/69 |
| 5,051,239 | 9/1991 | Von der Goltz | 422/73 |
| 5,339,830 | 8/1994 | Blake, III | 422/73 |
| 5,662,107 | 9/1997 | Sakariassen | 128/637 |
| 5,800,781 | 9/1998 | Gavin et al. | 422/73 |
| 5,854,423 | 12/1998 | Venegas | 73/64.41 |

FOREIGN PATENT DOCUMENTS 0 223 244  5/1987  European Pat. Off. .
0 316 599  5/1999  European Pat. Off. .

*Primary Examiner*—Jeffrey Snay
*Attorney, Agent, or Firm*—Jacobson, Price, Holman & Stern, PLLC

[57] ABSTRACT

A process and device are disclosed for measuring blood platelet aggregation or blood coagulation. The blood flows through an opening in a part and the occlusion of the opening is measured. The pressure fall ($\Delta P$) formed during occlusion of the opening is measured at predetermined time intervals (dt) and the volume flow (I) is changed to correspond to a predetermined function which simulates the flow resistance ($R_v$) of a capillary upstream of the opening. Alternatively, the pressure ($\Delta P$) is kept constant during the predetermined time intervals (dt) and afterwards, when the volume flow (I) has diminished by a certain value, the pressure is adjusted until it corresponds to the function.

12 Claims, 3 Drawing Sheets

PROCESS FOR MEASURING BLOOD PLATELET AGGREGATION OR BLOOD COAGULATION

The invention relates to a process for the measurement of the aggregation of blood platelets or the coagulation of blood according to the preamble of patent claim 1 and to a device for carrying out this process according to the preamble of patent claim 12.

The DE 35 41 057 C2 discloses such a process, in which blood is sucked into a capillary with the aid of a piston located in a cylinder, which is connected to the capillary and in which the actual pressure that prevails in the space between the piston and the aspirated blood is measured. This actual pressure is maintained at a desired value by moving the piston as a function of the difference between the actual pressure and a desired value. As a measure for the aggregation or the coagulation, the quantity of blood flow in the capillary is determined by detecting the movement of the piston.

One problem with such a process is the fact that the capillaries to be used are extremely difficult to produce, because the flow resistance of the capillary is a function of the fourth power of the radius of the capillary.

This is of the magnitude of 100 μm. This means that the capillaries must be produced with a very precise diameter. This requirement results in high costs. Another problem lies in the fact that the capillaries can clog, a state that leads to errors in the measurements. In addition, the interior surface of the capillary has to be of the highest quality and totally cleaned of foreign substances (e.g. grease), so that the blood platelets do not adhere, a state that would result in clogging or undesired effects on the flow. The outflow ends must be rounded so that the blood cells are not injured by shearing. In addition to the cost of production that is increased hereby, expenses are incurred by the requisite quality controls. Handling the capillaries with such small dimensions for further automatic processing is extremely difficult. The capillaries that result in the said drawbacks are, however, absolutely necessary due to physiological reasons, because they simulate the resistance of the arterioles. The preceding capillaries make the process of hemostasis more effective, because, when the aperture is open, the shear of a large flow is limited at the start of the measuring process and in this manner the interaction between the thrombocytes and the collagen is more effective.

Therefore, the object of the present invention is to provide a process and a device for the measurement of the aggregation of the blood platelets or the coagulation of the blood, in which process or with which device the problems attributable to the capillaries are avoided.

This problem is solved by a process with the features of patent claim 1 and by a system with the features of patent claim 12.

The essential advantage of the invention lies in the fact that the capillaries used in the prior art can be omitted, because those conditions, which are actually produced during the measurement with a capillary, are simulated by a volume flow/pressure control without capillary. The present device for the measurement of the aggregration of the blood platelets or the coagulation of the blood is advantageously significantly less expensive because the capillaries, which can be produced only quite expensively in the prior art, are superfluous.

In the following the invention and its embodiments are explained in detail with reference to the figures.

Figure 1:
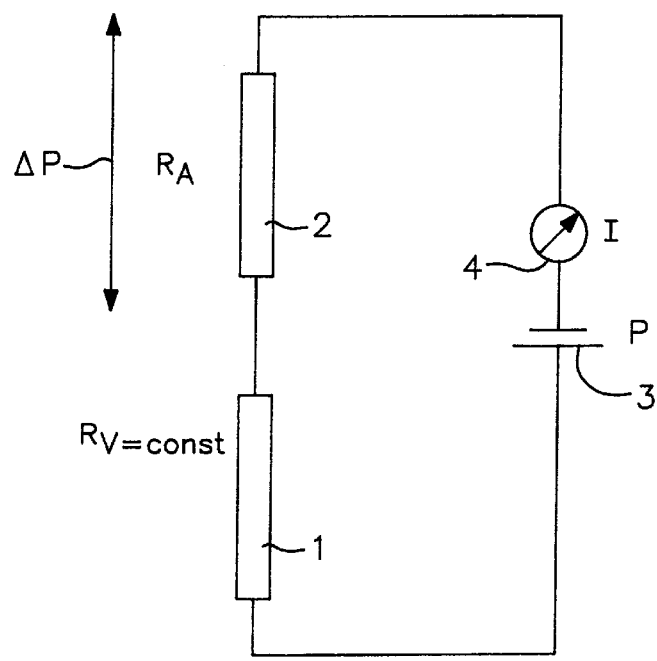
FIG. 1 depicts a circuit diagram in order to explain the process according to the invention.
Figure 3:
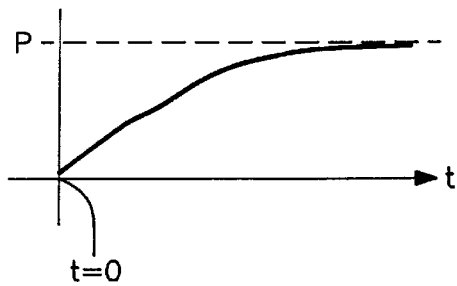
FIG. 3 depicts the time-dependent pressure curve at the aperture.

FIG. 1 shows the equivalent circuit diagram of a known device with a capillary, as known, for example, from the DE 35 41 057 C2. The flow resistance $R_v$ of the capillary, which is constant, is labelled 1. $R_A$ denotes the flow resistance 2 of the aperture; I, the volume flow; and P, the pressure, generated by a pressure source 3. The volume flow I is measured and displayed by a meter 4. At the flow resistance 2, representing the aperture, a drop in pressure ΔP is produced that depends on the clogging of the aperture or the thrombosis in the area of the same and rises starting from a minimum value (start of the measurement at time to) up to the value P of the pressure source 3 (clogging of the aperture), as shown in FIG. 3.

The volume flow quantity I is determined by the following equations:

$$I = \frac{P}{R_A + R_v} \quad (1)$$

$$I = \frac{\Delta P}{R_A} \quad (2)$$

ΔP denotes the drop in pressure at the aperture. This equation yields the flow resistance 2 of the aperture according to the following equation.

$$R_v = \frac{\Delta P}{I} \quad (3)$$

Substituting $R_A$ according to equation 3 into the equation 1 yields the pressure P according to the following relation:

$$P = \Delta P + R_v \cdot I \quad (4)$$

From this the following equation for the volume flow I can be derived:

$$I = \frac{P - \Delta P}{R_v} \quad (5)$$

Figure 2:
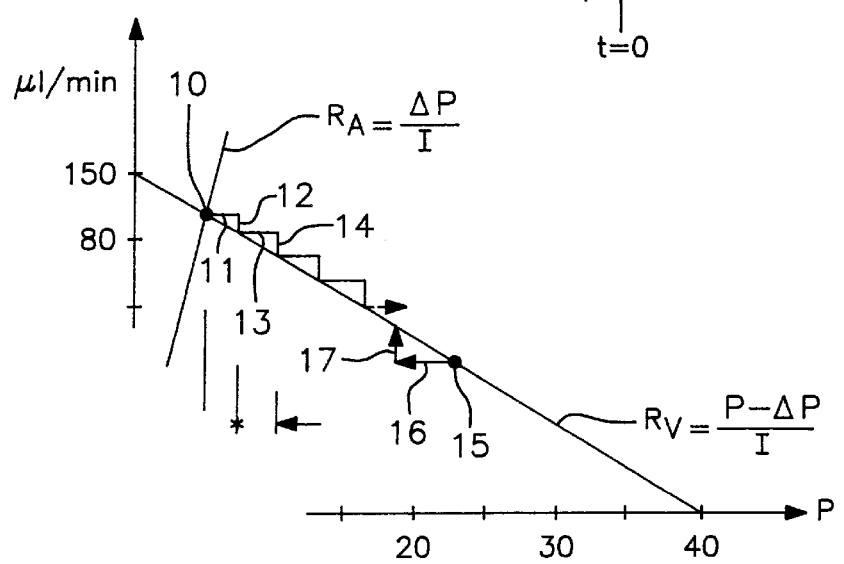
FIG. 2 depicts the dependence between the volume flow and the pressure in order to explain the process according to the invention.

FIG. 2 shows the characteristic lines $R_v$ and $R_{A(initial)}$ as a function of the pressure and the volume flow quantity. The functions $R_{A(initial)}$ and $R_v$ intersect at a point 10, which is equivalent to the working point just after the start of the measurement. At the start of the measurement the resistance $R_{A(initial)}$ of the unclogged aperture is known. It can be found by experiment on the basis of the dimensions of the aperture 2. Thus the characteristic line $R_A$ is established. The characteristic line $R_v$ follows from the dimensions of the capillary to be simulated, where at a pressure of, for example, 40 mm Hg the result is a volume flow of, for example, 150 μl/min. These characteristic lines are entered into a computer 50 (FIG. 4) and yield the intersecting point 10, which matches the conditions at the start of the measurement. When at this point the aperture 2 closes progressively, a corresponding rise in pressure ΔP can be detected. Then on the basis of the known characteristic line $R_v$ the computer 50 adjusts the volume flow I so far towards the bottom until I reaches a value corresponding to the characteristic line $R_v$. This procedure is repeated so often at specified time intervals until a specified volume flow, e.g. the volume flow of the value 0, is reached, a state that is equivalent to complete clogging of the aperture 2.

Inversely one may also proceed in such a manner that the control holds the pressure constant during a period of time, and thereafter when the volume flow has dropped by a specified amount, the pressure is readjusted until the characteristic line $R_v$ has been reached.

Figure 4:
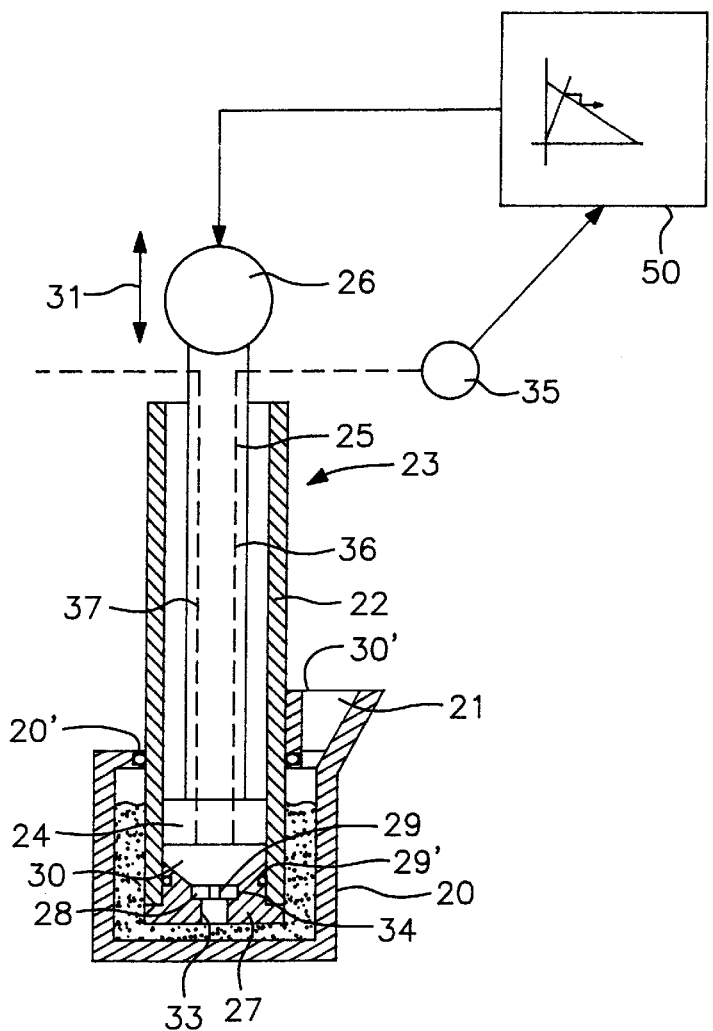
FIG. 4 depicts a device according to the invention in order to carry out the present process.

FIG. 3 shows, for example, that, starting from point 10, the pressure ΔP rises along the line 11 whereupon after a period of time dt the volume flow I is reduced so far along the line 12 by actuating the piston 24 in FIG. 4 by means of the drive 26 under control of the computer 50 until the characteristic line $R_v$ is reached again. After another rise in pressure ΔP (characteristic line 13) the volume flow is reduced again along the line 14 after a time period dt until the characteristic line $R_v$ is reached. This is continued until finally the value P at the volume flow quantity zero is reached.

When, for example, at a point 15 the pressure drops again along the line 16 due to the partial dissolving of the clogging in the aperture 2, the volume flow through the system is increased (line 17) until the characteristic line $R_v$ is reached again.

Due to this described, continuous approaching of the characteristic line $R_v$ the conditions that would exist with the presence of a capillary are accurately simulated in the present process.

At the start of the measurement the computer 50 can determine the characteristic line $R_{A(initial)}$ of the aperture 2 by itself. This takes place in a first step in that at a constant volume flow the pressure drop is measured with the aperture open. This is then also a measure for the blood viscosity.

According to FIG. 4, a first embodiment of the present device for carrying out the process described above comprises a blood reservoir 20, to which, for example, blood can be conveyed by way of a feed opening 21. At the same time the feed opening 21 is preferably closed by a membrane 30', which is penetrated by by the tip of the syringe in order to feed blood from a syringe or the like. This opening serves then to ventilate the chamber 30. Into the blood reservoir 20 the cylinder 22 of a syringe 23 is introduced, in whose interior there is a piston 24, which can be moved in the longitudinal direction of the cylinder 22 with the aid of a final control element 25, which can be actuated by a drive 26 (arrow 31). A sealing between the cylinder 22 and the blood reservoir 20 is accomplished with a seal 20'.

Into the bottom end of the cylinder 22, which is dipped into the blood reservoir 20, a holder 27 can be tightly inserted with the aid of a seal 29', the holder 27 exhibiting a passage opening 33, which empties on the side, facing the piston 24, into a recess 34, in which a part 28, exhibiting an aperture 29, is installed tightly in such a manner that the passage opening 33 precedes the aperture 29. Preferably the holder 27 and the part 28, exhibiting the aperture 29, are designed as a disposable part in the form of a small unit that is easy to handle. This accommodates the storage problems, which are caused by the relatively small refrigerators in the clinics. Between the part 28 with the aperture 29 and the piston 24 there is a chamber 30, which serves to receive the blood issuing through the aperture 29. The pressure, prevailing in the chamber 30, is measured by a sensor 35, which is shown schematicly. The corresponding connecting line to the chamber 30 is marked 36.

There is the possibility of bringing a specific liquid (e.g. NaCl or other substances) into the area of the aperture 29 by way of the line 37 before a measurement is made, in order to saturate the part 28, made preferably of a filter material (e.g. cellulose acetate). The liquid can be fed into the chamber 30 by way of a line 37. The said lines 36, 37 can run so as to be sealed through the piston 24 or the cylinder 22 to the chamber 30.

Before making a measurement, care is taken that the blood from the reservoir 20 is drawn into the the passage 33 by moving the piston 24 and thereafter through the aperture 29 into the chamber 30. The actual measurement can then start immediately or after a desired delay.

One important advantage of the embodiment of FIG. 4 lies in the fact that the measuring piston is coupled directly to the blood by way of the small air cushion of the chamber 30 without their being large reservoirs of air layered behind and interfering with the aperture 29, as in the case of the prior art. The said coupling enables that the blood flow follows without delay the movement of the piston; and thus the disturbing wetting resistances between blood, aperture and e.g. NaCl can be overcome immediately. Another feature, to keep the air chamber 30 as small as possible, consists of filling the sensor 35 and at least one part of the line 36 with preferably oil.

A rinsing liquid to rinse said chamber after making a measurement and before installing a new part 27 can be fed into the chamber 30 by way of the other line 37. In addition, air to dry the chamber 30 can be introduced.

Figure 5:
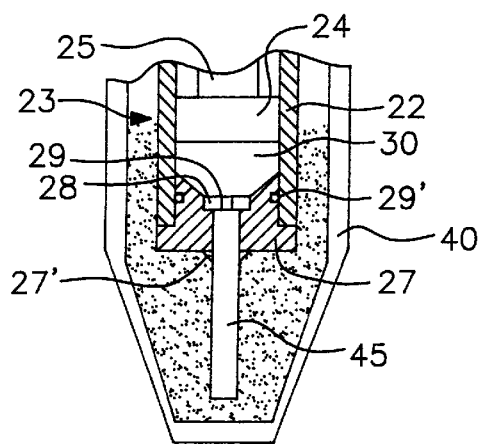
FIGS. 5 and 6 depict other devices to carry out the present process.

According to FIG. 5, a suction tube 45, preceding the aperture 29, projects into the blood reservoir 40. Preferably the tube extends into the passage 33 and is tightly connected, preferably cemented (reference numeral 27'), to the part 27. At the same time it must be pointed out that the tube 45 does not generate any significant hydrodynamic pressure and cannot be compared with the capillaries of the prior art, which, of course, the present invention is supposed to avoid. The tube 45, which can also be used in the embodiment of FIG. 4, also has another task, which is to represent the shear effects, from which the blood platelets suffer as they slid along the inner circumference of the arterioles. These mechanical shear processes, which can be important for different kinds of tests, can be simulated, in fact, only by providing the corporeal tube 45.

Preferably the blood can be removed by way of the tube 45 from a socalled vacutainer tube, which is closed by a penetrable stopper and contains the blood at subatmospheric pressure.

It must be pointed out that to simulate non-physiological processes the resistance of the capillary must be assumed to be nonlinear. It can also follow, for example, a quadratic function, according to which it increases faster toward the end of the measurement than at the start. For example, high stroke pressures to simulate the socalled Willebrand factor can play an important role during hemostatic processes.

Furthermore, it must be pointed out that, instead of the described aspiration of the blood from a reservoir 20 into the aperture 29, said blood can also be forced in the reversed direction from the cylinder chamber of the syringe 23 under pressure through the aperture.

Preferably the cylinder 22 and the blood reservoir 20 or 40 are made of plastic. They and preferably the holder 27, exhibiting the part 28 with the aperture 29, are designed together as a disposable part. At the same time this throwaway part may or may not include the tube 45. Furthermore, it is conceivable to integrate the piston 24 and optionally also the final control element 25 into the disposable part.

If the cylinder 22 is made, for example, of glass and is not integrated into the disposable part, it is rinsed automaticly together with the blood reservoir 20 or 40 after each measuring sequence. In this case only the holder 27 with the part 28 is designed as a throw-away part.

Figure 6:
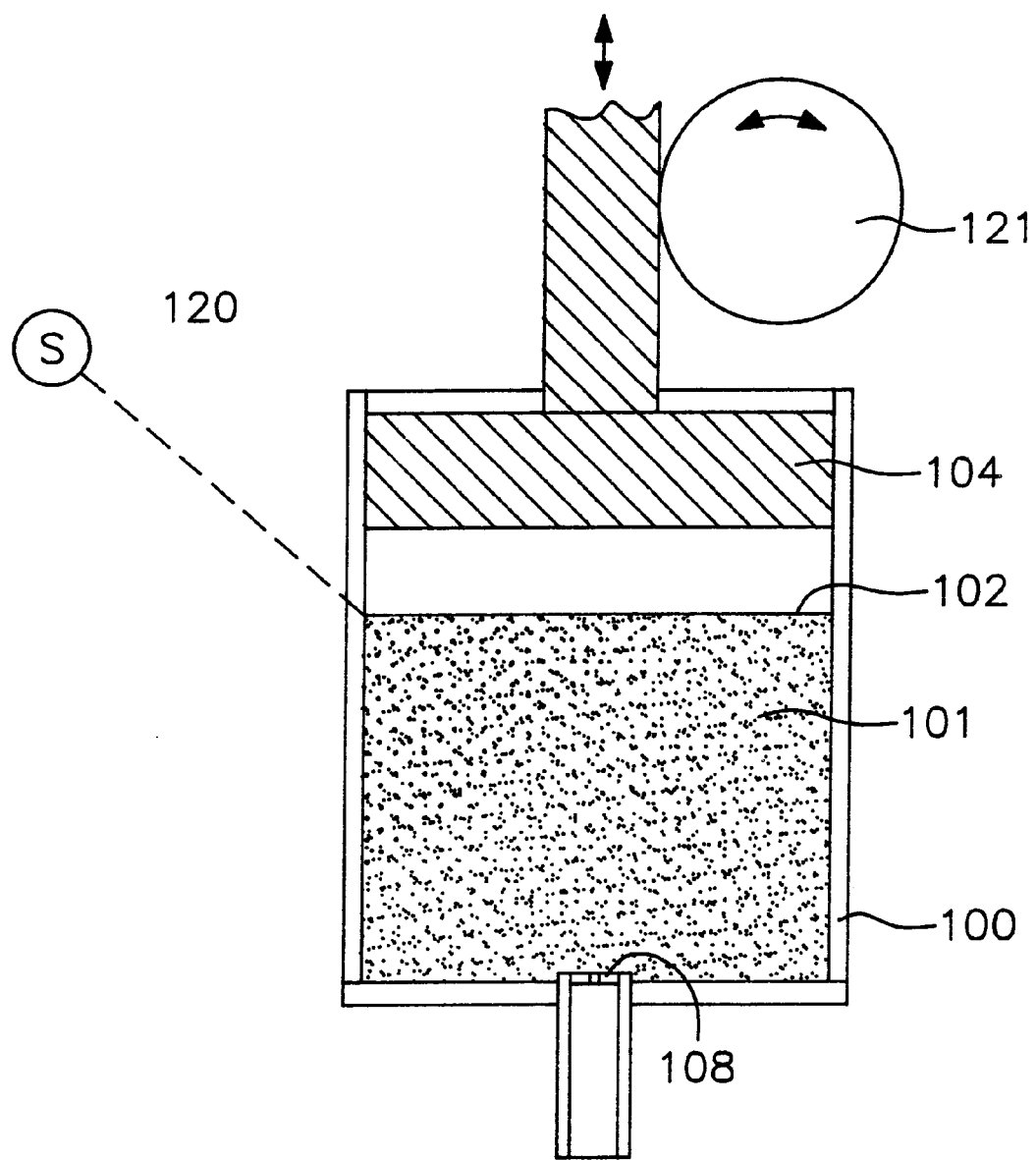

According to the schematic of FIG. 6, defined conditions are created when the blood 101 is forced out of a reservoir 100 through an aperture 108 in that the measurement is initiated only when the piston 104, pushing the blood, touches the surface of the blood 102. For this purpose there is a sensor 120 that generates a signal, which indicates the level of the blood surface 102 and which actuates an actuator 121 for the piston 104 in such a manner that said actuator moves the piston 104 until it touches the blood surface 102.

What is claimed is:

1. Process for the measurement of the aggregation of blood platelets or the coagulation of blood, in which process the blood flows through an aperture (29), containing a part (28), whereby the clogging of the aperture is measured, characterized in that the drop in pressure ($\Delta P$) occurring during the clogging is measured at specific time intervals (dt) at the aperture (29), and the volume flow (I) is changed in such a manner that it corresponds to a predetermined function, which simulates the flow resistance ($R_v$) of a capillary, preceding the aperture (29), or that during the predetermined time interval (dt) the pressure ($\Delta P$) is held constant and thereafter, when the volume flow (I) has decreased by an amount, is readjusted until it matches the function.

2. Process, as claimed in claim 1, characterized in that in a first step the resistance ($R_{A(initial)}$) of the aperture (29) is determined as the function of the dimensions of the aperture (29); that from the dimensions of the capillary to be simulated the flow resistance ($R_v$) is found; and that the measurement starts at a point (10), at which the characteristic lines ($R_{A(initial)}$ and $R_v$) intersect.

3. Process, as claimed in claim 1, characterized in that the blood is aspirated from a reservoir (20) directly into the aperture (29) with a piston/cylinder arrangement (23), which follows the aperture (29), into a chamber (30), preceding the piston (24) of the arrangement (23) in the cylinder (22) of the arrangement (23); that the pressure, prevailing in the chamber (30), is measured with a pressure sensor (35) and is entered into a computer (50), in which the characteristic lines ($R_{A(initial)}$ and $R_v$) are stored; and that to change the volume flow (I) the computer (50) moves with a drive the piston (24) in the cylinder (22) as a function of the pressure drop $\Delta P$, determined in the time interval (dt).

4. Process, as claimed in claim 1, characterized in that a stepping motor, which is coupled to the piston (24) by way of a final control element (25), is used as a drive (26).

5. Process, as claimed in claim 1, characterized in that a filter element, which contains the aperture (29), is used as the part (28).

6. Process, as claimed in claim 5, characterized in that a cellulose acetate filter is used as the filter element.

7. Process, as claimed in claim 1, characterized in that the filter element is wetted with a liquid before the measurement is initiated and the blood is aspirated into the aperture (29).

8. Process, as claimed in claim 7, characterized in that NaCl is used as the liquid.

9. Process, as claimed in claim 1, characterized in that the aperture (29) is preceded by a tube (35), which does not generate any significant hydrodynamic pressure and by way of which the blood is aspirated from the reservoir (40) to the aperture (29), whereby the tube simulates the sliding of the particles of blood along the inner circumferences of the arterioles.

10. Process, as claimed in claim 1, characterized in that the flow resistance ($R_v$) of the capillary is simulated by a linear characteristic line.

11. Process, as claimed in claim 1, characterized in that the flow resistance ($R_v$) of the capillary is simulated by a nonlinear characteristic line.

12. Process, as claimed in claim 1, characterized in that a piston (104), which can be moved by an actuator (121), forces the blood through the aperture (108) and that the measurement is started when the piston (104) touches the blood surface (102), detected by a sensor (120).

* * * * *